United States Patent [19]

Yahagi et al.

[11] Patent Number: 4,798,721

[45] Date of Patent: Jan. 17, 1989

[54] HAIR COSMETIC COMPOSITION COMPRISING SUBMICRON POLYMER PARTICLES

[75] Inventors: Kazuyuki Yahagi, Tokyo; Toshio Suzuki, Ichikawa, both of Japan

[73] Assignee: Kao Corporation, Tokyo, Japan

[21] Appl. No.: 902,651

[22] Filed: Sep. 2, 1986

[30] Foreign Application Priority Data

Sep. 13, 1985 [JP] Japan ................. 60-202898

[51] Int. Cl.$^4$ ............... A61K 4/06; A61K 7/09
[52] U.S. Cl. ........................... 424/70; 424/71; 428/402
[58] Field of Search ............ 428/402; 424/70, 71; 524/566, 577, 538, 839; 523/400

[56] References Cited

U.S. PATENT DOCUMENTS

| | | | |
|---|---|---|---|
| 3,574,822 | 4/1971 | Shepherd et al. | 124/71 |
| 3,660,561 | 5/1972 | Shepherd et al. | 424/71 |
| 3,784,391 | 1/1974 | Kruse et al. | 524/560 |
| 4,414,278 | 11/1983 | Cohen et al. | 428/402 |
| 4,460,569 | 7/1984 | Strosilla et al. | 424/70 |
| 4,542,069 | 9/1985 | Mauy et al. | 428/402 |
| 4,590,068 | 5/1986 | Berthet et al. | 428/402 |
| 4,644,041 | 2/1987 | Winnik et al. | 428/402 |
| 4,686,269 | 8/1987 | Tokunoga et al. | 428/402 |

Primary Examiner—Joseph L. Schofer
Assistant Examiner—Peter F. Kulkosky
Attorney, Agent, or Firm—Oblon, Fisher, Spivak, McClelland & Maier

[57] ABSTRACT

Novel hair cosmetic compositions comprising from 0.01 to 10% by weight of a particulate polymer having a weight average diameter of from 0.005 to 0.2 μm, said particulate polymer has a particle size distribution of such that the particles ranging from 0.005 to 0.2 μm in diameter are contained over 95% by weight and has a glass transition temperature, Tg, of over 300° K. As the particulate polymer, polymer latex such as polystyrene latex, vinyl homopolymer latex, polyurethane latex, epoxy resin latex and the like are preferably used.

The hair cosmetic compositions provide excellent hair style-forming/retaining property, good combing performance and good feeling of the treated hair. Further, they are free from easy separation which is inevitable for conventional compositions containing inorganic powder such as talc, mica and titanium.

10 Claims, No Drawings

HAIR COSMETIC COMPOSITION COMPRISING SUBMICRON POLYMER PARTICLES

BACKGROUND OF THE INVENTION

1. Field of the Invention

This invention concerns hair cosmetic compositions and more specifically such compositions containing a water-insoluble fine particulate polymer, having excellent style-forming or retaining performance of hair and further giving a favorable feeling to touch to the hair.

2. Description of the Prior Art

Hair style is one of most important factors in beauty cares, and various kinds of beauty treatments have been prevailed for making the style. For instance, hair may be wound and dried around curlers, or treated by a drier and brushes to make a style. In such hair cares, it is a usual practice that hair cosmetics such as set lotions, blowing agents, hair sprays and the like are used for the purpose of facilitating a style making or retaining the thus prepared hair style. Hair cosmetic compositions, therefore, are incorporated with polymers which are soluble in water or in organic solvents such as alcohols. Examples of such polymers are polyvinyl pyrrolidone, vinyl pyrrolidone/vinyl acetate copolymer, vinylpyrrolidone/vinyl acetate/alkylamino acrylate copolymer, methylvinyl ether/maleic anhydride copolymer, vinylacetate/chrotonic acid copolymer, copolymer of acrylic or methacrylic acid and acrylic or methacrylic acid esters. Hair styles have been formed or retained by the polymers spread or applied by way of aerosol to the hair.

However, conventional hair cosmetic compositions have disadvantages in that they necessitate a great amount of polymer materials to be deposited on the hair in order to retain the hair style. In addition, since the polymer materials deposited on the hair have a surface tension higher than the critical surface tension of the hair, they are deposited in the island-like small lumps on the hair, which leads to the stiff feeling of the hair and insufficient combing performance.

Hair rinses, hair treatment agents, etc. have been used after contaminations on the hair are removed by a shampoo in order to eliminate the unfavorable driness of the hair, to impart a soft touch to the hair and to obtain a smooth combing. However, since they contain cationic surface active agents or oily ingredients, although they can improve the softness and combing property of the hair, they are accompanied by drawbacks in that the hair becomes sticky and hair styles are difficult to be made or retained, thus improvement has been demanded therefor.

SUMMARY OF THE INVENTION

In view of the foregoing situations, the present inventors have made an earnest study for obtaining a hair cosmetic composition having an excellent hair style forming or retaining performance and, as a result, have accomplished this invention based on the finding that hair cosmetic composition capable of providing hair with an excellent style-forming or retaining effect without impairing the feelings of the hair and exhibiting favorable combing property can be obtained by blending a particular polymer with hair cosmetic compositions for shampoos, rinses, treatments, hair sprays, set lotions and the like.

Accordingly, this invention provides hair cosmetic compositions comprising from 0.01 to 10% by weight of a particulate polymer having a weight average diameter of from 0.005 to 0.2 $\mu$m, said particulate polymer has a particle size distribution of such that the particles ranging from 0.005 to 0.2$\mu$m in diameter are contained over 95% by weight and has a glass transition temperature, Tg, of over 300° K. It is preferred that the particulate polymer having the particle size as described above is used in the form of a polymer latex comprising that particulate polymer.

DETAILED DESCRIPTION OF THE INVENTION AND PREFERRED EMBODIMENTS

The polymer latex comprising the particulate polymer cannot be prepared by a conventional emulsion polymerizing process in that a polymerization is carried out in the presence of the emulsion of droplets of polymerizable monomers in the polymerization system.

According to this invention, the polymer latex is prepared by polymerizing a water-insoluble polymerizable monomer in a microemulsion or solubilized state. The microemulsion can be prepared by using a nonionic surface active agent and selecting a temperature appropriately near the phase transition temperature, or by combining the anionic surface active agent with an appropriate auxiliary surface active agent such as a higher alcohol or nonionic surface active agent. Further, the solubilized state can be obtained by using a great amount of a surface active agent relative to the polymerizable monomer.

Among them, most preferred is a process of conducting a polymerization in the state of the microemulsion using a nonionic surface active agent, setting the polymerizing temperature near the phase transition temperature and the interfacial tension between the monomer and water to not more than 1 dyne/cm and, preferably, not more than 0.5 dyne/cm.

The process for preparing the polymer latex used in the invention will be explained together with polymerizable monomers usable for the preparation.

(1) Addition-polymerized polymer latex:

Addition-polymerized latex can be obtained by polymerizing a polymerizable monomer while maintaining the microemulsion of an aqueous solution of a surface active agent having an interfacial tension between the monomer and water of less than 1 dyne/cm, in which the polymerizable monomer is solubilized within micelles formed by the surface active agent.

As the polymerizable monomer, any of known monomers usable in the emulsion polymerization can be used, which include ethylene unsaturated monomers such as ethylene, propylene, isobutene and butene-1; aromatic vinyl monomers such as styrene,$\alpha$-methylstyrene, vinyl toluene, halogenated styrene and divinyl benzene; acrylic esters having from 1 to 20 carbon atoms in the alkyl group such as ethyl acrylate, butyl acrylate and 2-ethylhexyl acrylate; methacrylate having from 1 to 20 carbon atoms such as methyl methacrylate, butyl methacrylate and lauryl methacrylate; vinyl esters such as vinyl acetate and vinyl propionate; vinyl ethers having from 1 to 20 carbon atoms such as ethyl vinyl ether and butyl vinyl ether; vinyl ketones having from 1 to 20 carbon atoms such as methyl vinyl ketone and ethyl vinyl ketone; vinyl cyan monomers such as acrylonitrile and methacrylonitrile; halogenated vinyls and halogenated vinylidene such as vinyl chloride, vinyl bromide, vinylidene chloride and vinylidene bromide; and conjugated aliphatic dienes such as 1,3-butadiene and 2-methyl-1,3-butadiene. These monomers can be used solely or as a mixture of two or more of them. Further, any of the above-mentioned monomers can be subject to copolymerization with maleic anhydride, a water soluble monomer, styrene sulfonic acid (salt), vinyl naphthalene sulfonic acid (salt) or acrylic acid (salt).

The most preferred process for producing the addition polymerized latex is carried out by adding a surface active agent in a reaction vessel charged with water to prepare an aqueous solution, adding polymerizable monomers and, if required, an aqueous solution of a radical polymerization initiator thereto while stirring under heat near the temperature at which the micelles of the surface active agent cause the phase transition while maintaining such a state as the interface tension between the monomer and water is not more than 1 dyne/cm, preferably from 0 to 0.5 dyne/cm, thereby initiating polymerization and then gradually adding a polymerizable monomer such that the interfacial tension between the aqueous solution of the surface active agent and the monomer phase does not exceed the above-mentioned range.

The radical polymerization initiator suitably used herein can include, for example, persulfates such as potassium persulfate, sodium persulfate and ammonium persulfate; azo compounds such as mineral acid salt of 2,2'-azobis(2-amidino propane), azobis-cyanobuareric acid and alkali metal or ammonium salt thereof; and redox type initiators such as tartaric acid-hydrogen peroxide, Rongalit-peroxide and ascorbic acid-peroxide. Among them, 2,2'-azobis(2-amidino propane) mineral acid salt is used preferably in the case of using the cationic surface active agent in the polymerization system and the persulfate is suitably used in other polymerization systems. The amount of the radical polymerization initiator is from 0.1 to 5 parts by weight and, preferably, from 0.1 to 3 parts by weight based on 100 parts by weight of the monomer constituting the polymer.

The reaction temperature is the highest temperature within the solubilizing region near the phase transition temperature, and a temperature within a range from 50° to 90° C. is preferred. While the time required for the polymerization varies depending on the type, composition and the concentration of the monomer, or the concentration of the radical polymerization initiator, polymerizing temperature, etc., the range from 5 to 50 hours is preferred.

In this way, a polymer latex containing a particulate polymer having an average particle size from 0.005 to 0.2 μm and in which 95% by weight or more of the particles have such a particle size range is obtained.

(2) Polycondensation latex

Polycondensation latex is obtainable by polymerizing a polycondensable monomer while maintaining the microemulsion of an aqueous solution of a surface active agent, which has an interfacial tension between the monomer and water of not more than 1 dyne/cm, and in which the polycondensable monomer is solubilized within the micelles formed by the surface active agent.

As the polycondensable monomer, any of known monomers usable in the interface polycondensation or low temperature polycondensation can be used. Among them, those monomers capable of forming polyamides or polyesters are preferred. For instance, the acid component for preparing the polyamide includes alkylene dicarboxylic acids comprising hydrocarbons having from 1 to 24 carbon atoms, phthalic acid such as dimeric acid, terephthalic acid and isophthalic acid, corresponding acid chlorides or acid anhydrides of aromatic polybasic carboxylic acids and cycloaliphatic polybasic carboxylic acids such as cyclohexyl dicarboxylic acid and, further, thioesters of dicarboxylic acids. Further, the amine component can include, for example, aliphatic polyamines comprising hydrocarbons of from 1 to 24 carbon atoms, for exampe, alkylene diamine and alkylene triamine, aromatic polyamides such as phenylene diamine and polyamines having heterocyclic ring such as 4,4'-diaminophenyl ether.

Further, the alcohol component in the case of preparing the polyester includes alkylene diols comprising hydrocarbons with from 1 to 24 carbon atoms, ethylene glycol condensate such as bis-β-hydroxyethyl terephthalate, aromatic polyhydric alcohols such as hydroquinone and bisphenol A, polyhydric alcohols such as glycerine derivatives. As the acid component, various compounds as described above can be mentioned.

The monomers are not restricted only to those as described above, and two or more of the monomers may further be used in admixture.

For practicing the polycondensation reaction, a surface active agent is added to a reactor charged with water for solubilizing the acid component by agitation. Thereafter, an aqueous solution of diamine or alcohol is added, or alternatively, solutions prepared by dissolving both of the components separately in organic solvents are solubilized in the respective aqueous solutions of the surface active agent and mixed. A solid monomer is preferably dissolved in an organic solvent and solubilized together with the solvent in micelles for conducting the polycondensation. In this case, any of water-insoluble solvents may be used and benzene, toluene, xylene or the like is preferably used. The reaction temperature is preferably at a temperature within the solubilizing region near the phase transition temperature and, generally, from −10° to 50° C. Further, while the reaction time varies depending on the type, composition and the concentratin of the monomer or the temperature, 2–60 minutes of time is usually preferred.

In this way, a polymer latex containing a particulate polymer having an average particle diameter from 0.005 to 0.2 μm, in which 95% or more of the particles have a diameter falled within this range can be obtained.

(3) Polyaddition polymerized latex

The polymer latex of polyaddition polymer is obtainable by polymerizing a monomer capable of polycondensation in a state where the monomer capable of polycondensation is solubilized in a plate-like micelles formed with the surface active agent, while using an aqueous solution of a surface active agent providing the interfacial tension between the monomer and water of not more than 0.5 dyne/cm and while maintaining the state of the microemulsion.

While all of known monomers usable in the ordinary polyaddition reaction can be used as the monomer capable of polyaddition, those monomers directed to polyurethanes, polyurea resins and epoxy resins are preferred.

The alcohol component for preparing the polyurethane includes those compounds having at least two hydroxy groups in one molecule, specifically, ethylene glycol, propylene glycol, butylene glycol, hexanediol, neopentyl glycol, polyethylene glycol, polypropylene glycol, polyoxytetramethylene glycol, glycerine, trimethylol propane and polyester having two or more terminal hydroxyl groups. Further, the isocyanate component includes those compounds having at least two isocyanate groups in one molecule, specifically, tolylene diisocyanate, xylylene diisocyanate, hexamethylene diisocyanate, 4,4'-diphenylmethane diisocyanate, triphenylmethane triisocyanate, trimethylol propane triisocyanate, polyesters, polyethers and polyurethanes having two or more terminal isocyanate groups.

The above-mentioned compounds can be used as the isocyanate component for producing polyurea, and the amine compounds includes those compounds having at least two amino groups in one molecule, specifically, hexamethylene diamine, dodecyldiamine, phenylene diamine, diaminodiphenyl ether and piperazine.

The epoxy component for preparing the epoxy resin includes those compounds having at least two epoxy groups in one molecule, specifically, diglycidyl ether compound of bisphenol A, glycidyl ester compound of dimeric acid and compounds prepared by oxidizing olefins. Further, the amine compounds as described above can be used as the amine component. Further, all of known hardners can be used, for example, tertiary amines, boron trifluoride-amine complex and imidazole, as well as amines, polyamines, carboxylic acid anhydrides, polysulfides, dicyandiamides and diisocyanates having functional groups capable of polyaddition reaction with the epoxy groups.

The polyaddition reaction is carried out as follows. In order to prepare the polyurethane or polyurea, a surface active agent is added to a reactor vessel charged with water thereby solubilizing the isocyanate ingredient under stirring. Next, an aqueous solution of diol or diamine is added thereto, or alternatively solutions of both of the ingredients dissolved separately in an organic solvent are solubilized in the aqueous soltions of the surface active agent and mixed the two. In order to prepare the epoxy resin, a solution of a prepolymer or a combination of terminal epoxy compound and various hardners dissolved in a solvent is added dropwise to the heated aqueous solution of the surface active agent.

In the case where the monomer is solid or highly viscous liquid, it is preferred to first dissolve the monomer in an organic solvent before carrying out the polyaddition reaction in micelles. Any of inert solvents insoluble in water and not reactive with any of the ingredients may be used as the organic solvent, and benzene, toluene, xylene, etc. are particularly preferred. The reaction temperature is selected within a solubilizing region near the phase transition temperature and, usually, it is preferably from 20° to 70° C. Further, while the reaction time varies depending on the kind, composition and the concentration of the monomer, or the temperature etc., it is preferably from 1 to 50 hours.

The phenol resin which is a polycondensate can be prepared in the same manner as employed for the epoxy resin described above. It can be prepared by using phenol derivative such as phenol or cresol and formaldehyde. In addition, a resol resin or novolak resin may be used, which is hardened by acid or polyamine.

The latex thus obtained contains particulate polymer having an average particle size from 0.005 to 0.2 μm and 95% by weight or greater of the particles have a particle size within the above-mentioned range. The average particle size of the polymer used in this invention is from 0.005 to 0.2 μm and, more preferably, from 0.01 to 0.1 μm converted from the weight value. Further, 95% by weight or greater of the polymer particles have the particle size within the range from 0.005 to 0.2 μm. When the polymer is incorporated into hair cosmetic compositions, the depositing property to the hair is degraded and no substantial effect for style-forming or retaining effect can be recognized if the particle size is too large or too small. Accordingly, those latexes used as a clouding agent to cream shampoos or the like cannot produce the effect of this invention because their average particle size is greater than 0.2 μm and they have a broader range of the particle size distribution.

The polymer used in this invention has a glass transition temerature (Tg) of higher than 300° K. If the glass transition temperature is lower than the above-mentioned value, the latex shows poor styleforming/retaining effect if it should deposit to the hair. The polymers having glass transition temperature (Tg) of higher than 300° K. include polymers of vinyl monomers such as polystyrene, polyvinyl acetate, polydivinyl benzene, polymethyl methacrylate; polyamides such as 6,12-nylon; polyurethanes such as polyaddition polymer of polypropylene glycol (average molecular weight of 1000) and xylene diisocyanate; and epoxy resins such as polyaddition polymer of bisphenol A and diglycidyl ether. The vinyl monomers can be added with other monomers in such an extent as not rendering the glass transition temperature (Tg) below 300° K.

Among the polymers, most preferred are those polystyrenes and copolymers of styrene and a vinyl monomer other than styrene that have glass transition temperature (Tg) of higher than 300° K.

The hair cosmetic compositions according to this invention are prepared by blending the polymer obtained as described above directly with a substrate material of the hair cosmetic compositions, or by blending a liquid suspension of the polymer previously concentrated to a desired concentration with the substrate. In the case of the preparation of aqueous hair cosmetic compositions, it is preferred to add the polymer to water before blending with other ingredients such as a thickner. The polymer is preferably blended into the hair cosmetic compositions within a range from 0.01 to 10% by weight and, more preferably, from 0.05 to 5% by weight calculated as the residue after water is removed.

Further, a long-chain alkyl quaternary ammonium salt and oils and fats can be incorporated into the hair cosmetic composition according to this invention in order to provide the hair with more favorable feelings. The long-chain alkyl quaternary ammonium salt can include those long-chain alkyl quaternary ammonium salts represented by the following general formula (I):

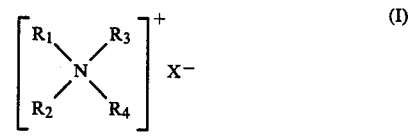

(I)

wherein one or two of $R_1$–$R_4$ represent a linear or branched long chain alkyl group having 8 to 24 carbon atoms and the remaining portion thereof represent alkyl or hydroxy alkyl group having 1 to 3 carbon atoms or benzyl group and X represents a halogen atom or an alkyl sulfate group having 1 or 2 carbon atoms, and they may be used alone or in admixture of two or more of them. Among the long chain alkyl quaternary ammonium salts represented by the foregoing formula (I), those having branched long chain alkyl groups may be synthesized by a known method starting from a branched higher fatty acid or branched higher alcohol. This starting materials may be of natural or synthetic products. The natural starting material can include lanolin fatty acids such as iso acid and anti-iso acid and terpene alcohols such as farnesol. The synthetic starting material can include oxoalcohol prepared by the oxo process, or Guerbet alcohol or 2-alkyl alkanol obtained through Guerbet condensation or aldol condensation starting from alcohol or aldehyde. For instance, in the case of oxo alcohol, the rate of branching compound of the resultant higher alcohol is small when starting from α-olefin, the rate of branching compound is increased in the case of the internal olefin and the rate of branching compound is increased to 100% in the case of branched olefin.

Among the branched type long chain alkyl quaternary ammonium salts, preferred are those having, as the branched alkyl group, 2-methylalkyl group represented by the following general formula (II):

$$R-\overset{CH_3}{\underset{|}{CH}}-CH_2- \qquad (II)$$

wherein R represents a linear alkyl group having 5 to 13 carbon atoms and preferred examples of the group include 2-methyloctyl, 2-methyldecyl, 2-methylundecyl, 2methyldodecyl, 2-methyltridecyl, 2-methyltetradecyl, 2-methylheptadecyl, etc. These 2-methyl alkyl groups are usually derived from oxo alcohol which is generally obtained as a mixture of linear-chain alcohols.

Those branched type long chain alkyl quaternary ammonium salts having these branched alkyl groups include alkyltrimethyl ammonium chloride, dialkyldimetyl ammonium chloride, alkyldimethyl benzyl ammonium chloride, alkyltrimethyl ammonium bromide, alkyltrimethyl ammonium methosulfate and dialkylmethyl hydroxymethyl chloride. Among them, particularly preferred are those having the 2-methylalkyl group represented by the formula (II), which examples are branched long chain monoalkyl quaternary ammonium salt such as 2-methyldecyltrimethyl ammonium chloride, 2-methyldodecyltrimethyl ammonium chloride, 2methyltetradecyltrimethyl ammonium chloride; branched long chain dialkyl quaternary ammonium salt in which one of the long chain alkyl group is branched such as 2-methyldecylundecyldimethyl ammonium chloride, 2-methyldodecyltridecyldimethyl ammonium chloride, 2-methyltetradecylpentadecyldimethyl ammonium chloride; and branched long chain dialkyl ammonium salts in which both of the long chain alkyl groups are branched such as di(2-methyldecyl)dimethyl ammonium chloride, di(2-methyldodecyl)dimethyl ammonium chloride and di(2-methyl tetradecyl)dimethyl ammonium chloride.

Further, examples of linear long chain alkyl groups can include, decyl, undecyl, dodecyl, tridecyl, tetradecyl, pentadecyl, hexadecyl, octadecyl, eicosanyl group and the like.

Those oils and fats generally employed can be used and they include liquid paraffins, glycerides, higher alcohols, lanolin derivatives, esters and higher fatty acid. Glycerides used are those mono-glyceride fatty acids derived from saturated or unsaturated linear or branched chains having from 12 to 24 carbon atoms. Among the oils and fats, those higher alcohols having linear or branched alkyl or alkenyl groups having 12 to 26 carbon atoms are particularly preferred and specific examples thereof include cetyl alcohol, stearyl alcohol, arachidic alcohol, behenyl alcohol, carnaubyl alcohol and ceryl alcohol.

The long chain alkyl quaternary ammonium salts and oils and fats are preferably incorporated within a range from 0.01 to 20% and from 0.1 to 30%, respectively.

When 0.01 to 10 wt % of casein or a casein derivative is incorporated into a hair cosmetic composition of the present invention, the hair styleforming/retaining effect is further enhanced without impeding feel to the touch of the hair. The casein derivatives include metal salts of casein, hydrolysates of casein and the like. A sodium salt and a hydrolysate having an average molecular weight of 1,000 to 50,000 are preferable as the metal salt of casein and the hydrolysate of casein, respectively.

The hair cosmetic compositions that can provide excellent effects due to the incorporation of the polymer and, if required, long chain alkyl quaternary ammonium salt and oils and fats in this invention have no particular restriction and they can include, for example, shampoos, hair rinses, hair conditioners, hair treatments, blowers, hair setting agents, hair liquids, hairtonics, brushing agents, hair sprays and hair colors. Further, there are no particular restrictions for the formulations of hair cosmetic compositions that can be blended with the polymer and they can include, for example, an aqueous solution, ethanol solution, emulsion, suspension, gel, solid-form, aerosol, powder and the like.

The hair cosmetic compositions according to this invention are excellent in the style-forming/retaining effect, depositing property, feeling, and can impart excellent style-forming/retaining ability and favorable touch to the hair. Further, they are free from the drawbacks such as easy separation and poor combing, when incorporated in a hair cosmetic composition, as compared with inorganic powder such as talc, mica and titanium easily available as a fine powder.

This invention will now be explained referring to Synthesis Examples and Examples.

SYNTHESIS EXAMPLES

Latexes were prepared by the Methods 1-8 shown below and the average particle size and the glass transition temperature Tg were determined and shown in Table 1. The average particle size was measured by a sub-micron particle analyzer "Coultar Model N-4" and represented by the average weight value. Tg was determined according to Polymer Handbook (A Wiley-Interscience Publication, John Wiley & Sons Inc., 1975).

Method 1

Polystyrene Latex A

A separable flask made of glass and equipped with a stirrer was charged with 500 parts by weight (hereinafter referred to simply as parts) of distilled water, 25 parts of polyoxyethylene (30) nonylphenyl ether (numeral value in the parenthesis represents here and hereinafter the average number of addition mol of ethylene oxide) and 1.2 parts of ammonium persulfate. The flask was purged with nitrogen to remove all air and heated to 62° C. while stirring. 125 parts of styrene were dropped over 2 hours and polymerization was proceeded for further 6 hours to obtain polystyrene latex A.

Method 2

Polystyrene Latex B

A separable flask made of glass and equipped with a stirrer was charged with 500 parts of distilled water, 15 parts of polyoxyethylene(30) nonylphenyl ether, 0.5 parts of ammonium persulfate and 0.5 parts of sodium sulfite. The flask was purged with nitrogen to remove all air and heated to 45° C. while stirring. 50 parts of styrene were dropped over one hour and polymerization was proceeded for further 8 hours to obtain polystyrene latex B.

Method 3

Polystyrene Latex C

Polystyrene latex C was prepared in the same manner as in the Method 2 excepting for lowering the reaction temperature to 35° C.

Method 4

Vinyl Homopolymer Latex

Various kinds of vinyl homopolymer latexes were obtained by using polyoxyethylene(30) nonylphenyl ether as the surface active agent, vinyl acetate monomer, methyl methacrylate monomer, n-butyl acrylate monomer, n-butyl methacrylate monomer or 2-ethylhexyl methacrylate monomer as the monomer and in the same manner as in the Method 1.

Method 5

Nylon Latex

In each of two beakers, 13 parts of polyoxyethylene(30) nonylphenyl ether and 200 parts of water were charged and stirred. A solution of 2 parts of dodecyldiamine dissolved in toluene was added to one (solution A) of the thus obtained aqueous solutions, while 1.8 parts of adipic dichloride was added to another solution (solution B) and they were stirred respectively. Both of the thus obtained transparent solubilized solutions were mixed under stirring at a room temperature and, after adjusting the pH to about 10 by using 5N-NaOH, reacted for several hours to obtain 6,12-nylon latex.

Method 6

Polyurethane Latex

In each of two beakers, 13 parts of polyoxyethylene(30) nonylphenyl ether and 200 parts of water were charged and stirred. A solution of 25 parts of polypropylene glycol (average molecular weight 1000) dissolved in toluene was added to one (solution A) of the thus obtained aqueous solution, while 5 parts of xylylene diisocyanate was added to another solution (solution B) and they were stirred respectively. After mixing these two solutions at room temperature, the mixed solution was stirred for two hours to obtain polyurethane latex.

Method 7

Epoxy Resin Latex

An aqueous solution containing 12 parts of polyoxyethylene(30) nonylphenyl ether dissolved in 200 parts of water was heated to 60° C., to which was added a solution of 2 parts of diglycidyl ether of bisphenol A dissolved in 8 parts of toluene, followed by stirring. 0.3 parts of dodecyl diamine was further added to the solubilized solution and reacted for further 4 hours at the same temperature to obtain an epoxy resin latex.

Method 8

Styrene Copolymer Latex

A styrene copolymer latex was obtained by the method according to the preparation process for the polystyrene latex shown in the Method 1 by using the same polyoxyethylene(30) nonylphenyl ether as the surface active agent, and replacing styrene with a mixture of styrene and various kinds of monomers (vinyl acetate monomer, sodium styrene sulfonate monomer, trimethylaminoethyl methacrylate chloride monomer).

The glass transition temperature, the average particle size and the ratio of particles having the particle size from 0.005 to 0.2 μm for the latexes obtained in the Methods 1–8 of the Synthesis Examples are collectively shown in Table 1.

EXAMPLE 1

A hair treatment composition was prepared by adding water to each of the polymer latexes obtained in the Methods 1–8 of the Synthesis Examples so as to have 1% by weight of the polymer material. Each composition was then tested for the following items and the results are shown in Table 2. Further, a hair rinse composition comprising 2% by weight of stearyl trimethyl ammonium chloride, 2% by weight of cetanol, 1% by weight of polymer latex (polymer content) and the balance of water was prepared, the performance was evaluated in the same manner. The results are shown in Table 3.

(1) Combing Force 20 g of human hair was wetted with water at 40° C. to be impregnated with 10 g of water content. The hair was treated for 30 sec by using 2 g of a test solution shown in Table 2 and then rinsed for 30 sec in running water at 40° C. After draining, the hair was dried by a dryer, left for one night in a thermostable and humidity stable chamber at 20° C. and 65% RH, set to a strain gage and then applied with combing in which a force exerted on the comb was measured.

(2) Style-Forming/Retaining Effect

A bundle of hair weighing 5 g and 20 cm long was treated for one minute with each of the test solutions shown in Table 2, rinsed and then wound around a glass tube of 1 cm diameter. Then the hair was left for one night in a thermostable and humidity stable chamber at 20° C. and 65 RH%, air dried and detached from the glass tube and then the length of the curl was measured with the elapse of time. The curl retainability was calculated from the result by using the following equation and the style-forming/retaining effect was examined by the following evaluation criteria.

$$\text{Curl retainability (\%)} = \frac{L_0 - L_B}{L_0 - L_A} \times 100$$

$L_0$: 20 cm
$L_A$: Curl length (cm) just after detaching from the glass tube.
$L_B$: Curl length 12 hours after detaching from the glass tube.

| Style-forming/retaining effect | Curl retainability (%) |
| --- | --- |
| ○ | between 65 and 100 |
| Δ | between 50 and 65 |
| X | between 0 and 50 |

(3) Depositing Property to Hair

Hair of 20 cm long and 50 μm in diameter was treated and dried in the same manner as described in (1) above. The hair was observed under a scanning electron microscope and the state of the fine polymer particles deposited to the surface of the hair was evaluated by the following evaluation criteria. Evaluation criteria:

| Deposition property | State on the Hair Surface |
| --- | --- |
| A | Deposits found substantially over the entire surface |
| B | Deposits found partially |
| C | Deposits found slightly |
| D | No deposits found at all |

(4) Feeling

A bundle of Japanese virgin hair was treated by the test solutions shown in Table 2 by the method as described in (1) above and then air-dried. The bundle of hair was evaluated for the feeling at five steps by 20 female members. The criterion for the evaluation was given as good (score 5), rather good (scre 3), ordinary (score 3), somewhat poor (score 2) and poor (score 1) and the results were expressed as the geometrical mean.

TABLE 1

| Polymer latex | Synthesis method | Glass transition temp. (°K.) | Average particle size (μm) | Particles having particle size of 0.005–0.2 μm (wt %) |
| --- | --- | --- | --- | --- |
| A. Polystyrene A | Method 1 | 373 | 0.066 ± 0.008 | 100 |
| B. Polystyrene B | Method 2 | 373 | 1.2 ± 0.1 | 0 |
| C. Polystyrene C | Method 3 | 373 | 2.0 ± 0.5 | 0 |
| D. Polyvinyl acetate | Method 4 | 305 | 0.058 ± 0.008 | 100 |
| E. Polydivinyl benzene | Method 4 | 379 | 0.078 ± 0.007 | 100 |
| F. Polymethyl methacrylate | Method 4 | 378 | 0.063 ± 0.004 | 100 |
| G. Poly-n-butyl acrylate | Method 4 | 219 | 0.12 ± 0.01 | 98 |
| H. Poly-n-butyl methacrylate | Method 4 | 293 | 0.075 ± 0.004 | 100 |
| I. Poly-2-ethylhexyl methacrylate | Method 4 | 263 | 0.15 ± 0.02 | 96 |
| J. 6,12-nylon | Method 5 | 319 | 0.035 ± 0.005 | 100 |
| K. Polyurethane | Method 6 | 379 | 0.055 ± 0.006 | 100 |
| L. Epoxy resin | Method 7 | 393 | 0.047 ± 0.005 | 100 |
| M. Styrene/vinyl acetate (99/1) copolymer | Method 8 | 372 | 0.052 ± 0.003 | 100 |
| N. styrene/sodium styrene sulfonate (94/6) copolymer | Method 8 | 363 | 0.042 ± 0.005 | 100 |
| O. Styrene/trimethylaminoethyl methacrylate chloride (94/6) copolymer | Method 8 | 358 | 0.096 ± 0.007 | 100 |
| P. Styrene/vinyl acetate copolymer (commercial goods) | — | — | 0.2 ± 0.1 | 50 |
| Q. Styrene/vinyl pyrrolidone copolymer (commercial goods) | — | — | 0.5 ± 0.3 | 30 |
| R. Nylon (commercial goods) | — | — | 2.0 ± 0.5 | 0 |

TABLE 2

| Polymer latex | Combing force (g) | Style-forming retaining effect | Hair deposition | Feeling of treated hairs |
| --- | --- | --- | --- | --- |
| A. Polystyrene A | 200 | ○ | A | 3.0 |
| B. Polystyrene B | 265 | X | C | 1.2 |
| C. Polystyrene C | 220 | X | C | 2.0 |
| D. Polyvinyl acetate | 208 | ○ | A | 3.2 |
| E. Polydivinyl benzene | 207 | ○ | A | 2.6 |
| F. Polymethyl methacrylate | 205 | ○ | A | 2.7 |
| G. Poly-n-butyl acrylate | 210 | Δ | A | 1.8 |
| H. Poly-n-butyl methacrylate | 212 | Δ | A | 2.0 |
| I. poly-2-ethylhexyl methacrylate | 210 | Δ | A | 2.3 |
| J. 6,12-nylon | 165 | ○ | A | 3.7 |
| K. polyurethane | 178 | ○ | A | 3.5 |
| L. Epoxy resin | 210 | ○ | A | 2.5 |
| M. Styrene/vinyl acetate (99/1) copolymer | 203 | ○ | A | 3.0 |
| N. Styrene/sodium styrene sulfonate (94/6) copolymer | 196 | ○ | A | 2.4 |
| O. Styrene/trimethylaminoethyl methacrylate chloride (94/6) copolymer | 210 | ○ | A | 2.4 |
| P. Styrene/vinyl acetate copolymer (commercial goods) | 243 | X | C | 2.0 |
| Q. Styrene/vinylpyrrolidone copolymer (commercial goods) | 238 | X | C | 2.4 |
| R. Nylon (commercial goods) | 220 | X | C | 2.2 |
| S. None (control) | 200 | X | D | 1.2 |

TABLE 3

| Polymer latex | Combing force (g) | Style-forming retaining effect | Hair deposition | Feeling of treated hairs |
| --- | --- | --- | --- | --- |
| A. Polystyrene A | 96 | | A | 4.5 |

TABLE 3-continued

| Polymer latex | Combing force (g) | Style-forming retaining effect | Hair deposition | Feeling of treated hairs |
|---|---|---|---|---|
| B. Polystyrene B | 118 | X | C | 2.5 |
| C. Polystyrene C | 100 | X | C | 4.0 |
| D. Polyvinyl acetate | 105 | | A | 4.2 |
| E. Polydivinyl benzene | 97 | | A | 3.7 |
| F. Polymethyl methacrylate | 97 | | A | 4.0 |
| G. Poly-n-butyl acrylate | 93 | Δ | A | 3.0 |
| H. Poly-n-butyl methacrylate | 95 | Δ | A | 3.1 |
| I. Poly-2-ethylhexyl methacrylate | 97 | Δ | A | 2.9 |
| J. 6,12-nylon | 90 | | A | 4.5 |
| K. Polyurethane | 92 | | A | 4.5 |
| L. Epoxy resin | 103 | | A | 3.8 |
| M. Styrene/vinyl acetate (99/1) copolymer | 92 | | A | 4.6 |
| N. Styrene/sodium styrene sulfonate (94/6) copolymer | 105 | | A | 4.2 |
| O. Styrene/trimethylaminoethyl methacrylate chloride (94/6) copolymer | 103 | | A | 4.1 |
| P. Styrene/vinyl acetate copolymer (commercial goods) | 123 | X | C | 3.1 |
| Q. Styrene/vinylpyrrolidone copolymer (commercial goods) | 117 | X | C | 3.5 |
| R. Nylon (commercial goods) | 110 | X | C | 3.4 |
| S. None (control) | 131 | X | D | 2.5 |

As apparent from Tables 2 and 3, all of the hair cosmetic composition comprising polymer latexes according to this invention were highly depositing to hair and show preferable style-forming/retaining effects even when using the polymer latex along.

EXAMPLE 2

Shampoo Composition

| (Formulation) | |
|---|---|
| A Sodium salt of polyoxyethylene (2.5) lauryl ether sulfate | 15 (%) |
| B Coconut fatty acid diethanol amide | 3 |
| C Polystyrene latex A (obtained by Method 1 of the Synthesis Example, polymer content: 20%) | 2 |
| D Perfume | 0.5 |
| E Colorant | slight amount |
| F Citric acid | slight amount |
| G Water | balance |

(Preparation Method)

The ingredient C was uniformly dispersed into the ingredient G under stirring at room temperature, the ingredients A and B were added and uniformly dissolved and then the ingredients D, E and F were incorporated into the solution to provide excellent style-forming and retaining property and favorable feeling thereby obtain a uniform and stable shampoo composition.

EXAMPLE 3

Hair Rinse Composition

| (Formulation) | |
|---|---|
| A Distearyldimethyl ammonium chloride | 2 (%) |
| B Propylene glycol | 3 |
| C Styrene/vinyl acetate (99/1) copolymer latex (obtained by Method 8 of the Synthesis Example, polymer content: 20%) | 1 |
| D Perfume | 0.5 |
| E Colorant | slight amount |
| F Water | balance |

(Preparation Method)

The ingredient C was uniformly dissolved in the ingredient F and heated. A heated uniform solution of the ingredients A, B and C was added thereto under stirring followed by cooling and then ingredients D and E were incorporated to obtain a hair rinse composition capable of providing hair with an excellent styleforming/retaining property and favorable feeling.

EXAMPLE 4

Hair Conditioner Composition

| (Formulation) | |
|---|---|
| A Styrene/trimethylaminoethyl methacrylate chloride (94/6) copolymer latex (obtained by Method 8 of Synthesis Example, polymer content: 20%, average particle size: 0.096 ± 0.007 μm) | 1 (%) |
| B Methylparaben | 0.1 |
| C Ethanol | 10.0 |
| D Water | balance |
| E Perfume | 0.2 |

(Preparation Method)

The ingredient A was uniformly dispersed in the ingredient D under stirring at room temperature and then ingredients B and C and E were added to obtain a hair conditioner capable of providing hair with excellent style-forming/retaining property and favorable feeling.

EXAMPLE 5

Hair Set Composition

| (Formulation) | |
|---|---|
| A Epoxy resin (obtained by Method 7 of Synthesis Example, polymer content: 20%) | 2 (%) |
| B Ethanol | 10 |
| C Water | balance |
| D Hydroxyethylcellulose | 0.2 |
| E Perfume | 0.2 |

(Preparation Method)

The ingredient A was uniformly dispersed in the ingredient C under stirring at room temperature and then ingredients B, D and E were added to obtain a hair set composition capable of providing hair with an excellent style-forming/retaining property and favorable feeling.

EXAMPLE 6

Hair Liquid Composition

| (Formulation) | | |
|---|---|---|
| A | Styrene/sodium styrene sulfonate (94/6) copolymer latex (obtained by Method 8 of Synthesis Example, polymer content: 20%) | 1 (%) |
| B | Polyoxypropylene (30) butyl ether | 15.0 |
| C | Ethanol | 40.0 |
| D | Water | balance |
| E | Perfume | 0.3 |

(Preparation Method)

The ingredient A was dispersed in the ingredient D under stirring at room temperature and then ingredients B, C and E were added and mixed well, to obtain a hair liquid composition capable of providing hair with an excellent style-forming/retaining property and favorable feeling.

EXAMPLE 7

Hairtonic Composition

| (Formulation) | | |
|---|---|---|
| A | Styrene/sodium styrene sulfonate (94/6) copolymer latex (obtained by Method 8 of Synthesis Example, polymer content: 20%) | 1 (%) |
| B | PCA-A1 | 0.5 |
| C | Ethanol | 55.0 |
| D | Water | balance |
| E | Perfume | 0.3 |

(Preparation Method)

The ingredient A was uniformly dispersed in the ingredient D under stirring at room temperature and then ingredients B, C and E were added and well mixed to obtain a hairtonic composition capable of providing hair with an excellent style-forming/retaining property and favorable feeling.

EXAMPLE 8

Hair Brushing Composition

| (Formulation) | | |
|---|---|---|
| A | Styrene/vinyl acetate (99/1) copolymer latex (obtained by Method 8 of Synthesis Example, polymer content: 20%) | 1 (%) |
| B | Ethanol | 10.0 |
| C | Polyethylene glycol 6000 | 3.0 |
| D | Water | balance |
| E | Perfume | 0.2 |

(Preparation Method)

The ingredients A-E where sufficiently dispersed in the ingredient D and stirred well to obtain a hairbrushing composition capable of providing hair with an excellent style-forming/retaining property and favorable feeling.

EXAMPLE 9

Blow Finishing Composition

| (Formulation) | | |
|---|---|---|
| A | Stearyltrimethyl ammonium chloride | 0.4 (%) |
| B | Polyethylene glycol | 0.1 |
| C | Perfume | 0.3 |
| D | Water | balance |
| E | Polystyrene latex A (obtained by Method 1 of Synthesis Example, polymer content: 20%; particle size 0.1 ± 0.01 μm) | 0.5 |

(Preparation Method)

The ingredient E was uniformly dispersed in the ingredient D under stirring and then ingredients A, B and C were added to obtain a blow finishing composition capable of providing hair with an excellent style-forming/retaining property and favorable feeling.

EXAMPLE 10

Aerosol Type Hair Set Composition

| (Formulation) | | |
|---|---|---|
| A | Styrene/trimethylaminoethyl methacrylate chloride (94/6) copolymer latex (obtained by Method 8 of Synthesis Example, polymer content: 20%) | 1 (%) |
| B | Silicone oil | 1 |
| C | Perfume | 0.1 |
| D | Anhydrous ethanol | balance |
| E | Furon 12 | 70 |

(Preparation Method)

Ingredients B and C were dissolved in the ingredient D and then the ingredient A was added and dispersed uniformly. They were packed in a aerosol can to which a Furon gases was filled to thereby obtain an aerosol type hair set composition capable of providing excellent style-forming/retaining property and favorable feeling.

EXAMPLE 11

Hair Rinse Composition

| (Formulation) | | |
|---|---|---|
| A | Distearyldimethyl ammonium chloride | 2.0 (%) |
| B | Stearyltrimethyl ammonium chloride | 1.0 |
| C | Cetyl alcohol | 2.0 |
| D | Liquid paraffin | 1.0 |
| E | Silicone oil | 0.5 |
| F | Propylene glycol | 3.0 |
| G | Styrene/vinyl acetate copolymer latex (obtained by Method 8 of Synthesis Example, polymer content: 20%) | 1.0 |
| H | Perfume | 0.5 |
| I | Colorant | slight amount |
| J | Water | balance |

EXAMPLE 12

Hair Treatment Composition (Formulation)

| | | |
|---|---|---|
| A | Isostearyltrimethyl ammonium chloride | 2.0 (%) |
| B | Liquid paraffin | 1.0 |
| C | Collagen decomposition product | 3.0 |
| D | Hardened castor oil | 1.0 |
| E | Polyoxyethylene hardened castor oil derivative (E060) | 0.5 |
| F | Styrene/trimethylaminoethyl methacrylate chloride copolymer latex (obtained by Method 8 of Synthesis Example, polymer content: 20%) | 1.0 |
| G | Methylparaben | 0.1 |
| H | Ethanol | 5.0 |
| I | Perfume | 0.2 |
| J | Water | balance |

EXAMPLE 13

Hair Set Composition (Formulation)

| | | |
|---|---|---|
| A | Cetostearyltrimethyl ammonium chloride | 1.0 (%) |
| B | Polyoxyethylene alkyl ether (E090) | 1.0 |
| C | Polyoxyethylene hardened castor oil derivative (E060) | 0.5 |
| D | Cetostearyl alcohol | 0.05 |
| E | Styrene/potassium methacrylate (95/5) copolymer latex (obtained by Method 8 of Synthesis Example, polymer content: 20%) | 2.0 |
| F | Ethanol | 10.0 |
| G | Hydroxyethylcellulose | 0.2 |
| H | Perfume | 0.2 |
| I | Water | balance |

EXAMPLE 14

Hair Liquid Composition (Formulation)

| | | |
|---|---|---|
| A | Stearyltrimethyl ammonium chloride | 0.05 (%) |
| B | Cetanol | 0.05 |
| C | Polyoxyethylene hardened castor oil derivative (E060) | 0.5 |
| D | Styrene/sodium styrene sulfonate (94/6) copolymer latex (obtained by Method 8 of synthesis Example, polymer content: 20%) | 1 |
| E | Polyoxypropylene(30) butyl ether | 15.0 |
| F | Ethanol | 40.0 |
| G | Perfume | 0.3 |
| H | Water | balance |

EXAMPLE 15

Blow Finishing Composition (Formulation)

| | | |
|---|---|---|
| A | Stearyltrimethyl ammonium chloride | 0.4 (%) |
| B | Cetyl alcohol | 0.02 |
| C | Polyoxyethylene alkyl ether (E020) | 0.5 |
| D | Polyethylene glycol | 0.1 |
| E | Perfume | 0.3 |
| F | Polystyrene latex A (obtained by Method 1 of Synthesis Example, polymer content: 20%) | 0.5 |
| G | Water | balance |

EXAMPLE 16

Aerosol Type Hair Set Composition (Formulation)

| | | |
|---|---|---|
| A | Stearyltrimethyl ammonium chloride | 0.5 (%) |
| B | Distearyldimethyl ammonium chloride | 0.5 |
| C | Styrene/trimethylaminoethyl methacrylate chloride (94/6) copolymer latex (obtained by Method 8 of Synthesis Example, polymer content: 20%) | 1.0 |
| D | Silicone oil | 1.0 |
| E | Perfume | 0.1 |
| F | Furon 12 | 70 |
| G | Anhydrous ethanol | balance |

EXAMPLES 17–19

Hair rinse compositions shown in Table 4 were prepared according to the usual manner. All of these compositions showed more excellent hair style-forming-/retaining effect compared with a hair rinse composition without containing casein or a casein derivative, and, at the same time, they exhibited good combing performance and good feeling of the treated hair.

TABLE 4

| | | Example | | |
|---|---|---|---|---|
| | | 17 | 18 | 19 |
| A | Stearyl trimethyl ammonium chloride | 2 wt % | 2 wt % | 2 wt % |
| B | Cetyl alcohol | | | |
| C | Polystyrene latex A (obtained by Method 1 of Synthesis Example, polymer content: 20%) | 1 | 1 | 1 |
| D | Casein | 1 | — | — |
| E | Sodium caseinate | — | 1 | — |
| F | Hydrolyzed casein (average m.w. = 10,000) | — | — | 1 |
| G | Water | balance | balance | balance |

What is claimed is:

1. A hair cosmetic composition comprising from 0.01 to 10% by wt. of a particulate latex polymer of water-insoluble monomers, said polymer selected from the group consisting of polystyrenes, copolymers of styrene with at least one vinyl monomer other than styrene, polyamides, polyurethanes, epoxy resins, and polymethyl methacrylates, wherein said particulate polymer has a weight average diameter of from 0.005 to 0.2 microns, particle size distribution such that greater than 95% by weight of the particles have a diameter ranging from 0.005 to 0.2 microns, and wherein said particulate ploymer has a glass transition temperature greater than 300 ® K.

2. A hair cosmetic composition comprising:
   (A) from 0.01 to 20% by wt. of at least one long chain alkyl quarternary ammonium salt having the formula:

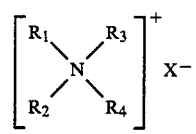

wherein one or two of $R_1$, $R_2$, $R_3$, and $R_4$ is a linear or branched $C_{8-24}$ alkyl group and the remaining R groups are independently a $C_{1-3}$ alkyl or hydroxy alkyl group or a benzyl group, and X is a halogen atom or a $C_{1-2}$ alkyl sulfate group;

(B) from 0.1 to 30% by wt. of oils and fats, and (C) from 0.01 to 10% by wt. of a particulate latex polymer of water-insoluble monomers, said polymer selected frrom the group consisting of polystyrenes, copolymers of styrene and at least one vinyl monomer other than styrene, polyamides, polyurethanes, epoxy resins, and polymethyl methacrylates, wherein said particulate polymers has a weight average diameter of from 0.005 to 0.2 microns, a particle size distribution such that greater than95% by wt. of the polymer particles are in the range of from 0.005 to 0.2 microns in diameter, and said particulate polymer has a glass transition temperature greater than 300° K.

3. The hair cosmetic composition of claim 1, wherein said vinyl monomer is selected from the group consisting of ethylenically unsaturated monomers, aromatic vinyl monomers, acrylic esters having $C_{1-20}$ carbon atoms in the alkyl group, $C_{1-20}$ vinyl ethers, $C_{1-20}$ vinyl ketones, vinyl cyano monomers, halogenated vinyl monomers, and conjugated aliphatic dienes.

4. The hair cosmetic composition of claim 1, wherein said vinyl monomer is selected from the group consisting of ethylene, propylene, isobutene, 1-butene, α-methylstyrene, vinyl toluene, halogenated styrene, divinyl benzene, ethyl acrylate, butyl acrylate, 2-ethylhexyl acrylate, methyl methyacrylate, butyl methyacrylate, lauryl methacrylate, vinyl acetate, vinyl propionate, ethyl vinyl ether, butyl vinyl ether, methyl vinyl ketone, ethyl vinyl ketone, acyrlonitrile, methacrylonitrile, vinyl chlroide, vinyl bromide, vinylidene chloride, vinylidene bromide, 1,3-butadiene and 2-methyl-1,3-butadiene.

5. The hair cosmetic composition of claim 2, wherein said vinyl monomer is selected from the group consisting of ethylenically unsaturated monomers, aromatic vinyl monomers, acrylic esters having $C_{1-20}$ carbon atoms in the alkyl group, $C_{1-20}$ vinyl ethers, $C_{1-20}$ vinyl ketones, vinyl cyano monomers, halogenated vinyl monomers, and conjugated aliphatic dienes.

6. The hair cosmetic composition of claim 2, wherein said vinyl monomer is selected from the group consisting of ehtylene, propylene, iosbutene, 1-butene, α-methylstyrene, vinyl toluene, halogenated styrrene, divinyl benzene, ethyl acryalte, butyl acrylate, 2-ethylhexyl acrylate, methyl methy acrylate, butyl methyacrylate, lauryl methacrylate, vinyl acetate, vinyl propionate, ethyl vinyl ether, butyl vinyl ether, methyl vinyl ketone, ethyl vinyl ketone, acrylonitrile, methacrylonitrile, vinyl chloride, vinyl bromide, vinylidene chlroide, vinylidene bromide, 1,3-butadiene and 2-methyl-1,3-butadiene.

7. The hair cosmetic composition of claim 1, wherein the weight average diameter of said particulate latex polymer is from 0.01 to 0.1 micron.

8. The hair cosmetic composition of claim 2, wherein the weight average diameter of said particulate latex polymer is from 0.01 to 0.1 micron.

9. The hair cosmetic composition of claim 1, wherein said particulate latex polymer is selected from the group consisting of polystyrene, polyvinylacetate, polydivinylbenzene, polymethylmethacrylate, poly-n-butylacrylate, poly-n-butylmethacrylate, poly-2-ethylhexylmethacrylate, 6,12-nylon, poyurethanes, epoxy resins, styrene/vinyl acetate copolymers, and styrene/trimethylaminoethyl methacrylate chlroide copolymers.

10. The hair cosmetic composition of claim 2, wherein said particulate latex polymer is selected from the group consisting of polystyrene, polyvinyl acetate, polydivinylbenzene, polymethylmethacrylate, poly-n-butylacrylate, poly-n-bytylmethacrylate, poly-2-ethylhexylmethacrylate, 6,12-nylon, polyurethanes, epoxy resins, styrene/vinyl acetate copolymers, and styrene/-trimethylaminoethyl methacrylate chloride copolymers.

* * * * *

UNITED STATES PATENT AND TRADEMARK OFFICE
CERTIFICATE OF CORRECTION

PATENT NO. : 4,798,721

DATED : September 2, 1986

INVENTOR(S) : Kazuyuki YAHAGI et al

It is certified that error appears in the above-identified patent and that said Letters Patent is hereby corrected as shown below:

Delete Claims 1,3,4,7, 9 and 10.

At Column 19, line 16, after "300°K" insert --, and (D) the balance being water--.

On The Title Page, "10 Claims" should read -- 4 Claims --.

Signed and Sealed this

Fifth Day of December, 1989

*Attest:*

JEFFREY M. SAMUELS

*Attesting Officer*  *Acting Commissioner of Patents and Trademarks*